United States Patent [19]

Volkamer et al.

[11] 4,278,504
[45] Jul. 14, 1981

[54] ISOLATION OF A CONJUGATED DIOLEFIN FROM A C$_4$- OR C$_5$-HYDROCARBON MIXTURE

[75] Inventors: Klaus Volkamer, Frankenthal; Klaus Bröllos, Seeheim; Alfred Lindner, Bobenheim-Roxheim; Ulrich Wagner, Limburgerhof; Hans-Martin Weitz, Bad Duerkheim; Klaus-Jürgen Schneider, Neustadt, all of Fed. Rep. of Germany

[73] Assignee: BASF Aktiengesellschaft, Fed. Rep. of Germany

[21] Appl. No.: 126,903

[22] Filed: Mar. 3, 1980

[30] Foreign Application Priority Data

Mar. 23, 1979 [DE] Fed. Rep. of Germany ....... 2911393

[51] Int. Cl.$^3$ .......................... B01D 3/40; C07C 7/08
[52] U.S. Cl. ........................................ 203/53; 203/56; 203/58; 203/60; 203/63; 585/810; 585/862; 585/865; 585/866
[58] Field of Search .................. 203/56, 53, 51, 63, 203/58, 60; 585/864–866, 810

[56] References Cited

U.S. PATENT DOCUMENTS

| | | | |
|---|---|---|---|
| 2,366,360 | 1/1945 | Semon | 203/56 |
| 2,455,803 | 12/1948 | Pierroti | 203/51 |
| 3,242,227 | 3/1966 | Kroeper et al. | |
| 3,436,438 | 4/1969 | Takao et al. | |
| 3,681,202 | 8/1972 | Funkhouser | 203/60 |
| 3,707,575 | 12/1972 | Muller et al. | 203/60 |
| 4,076,595 | 2/1978 | Haskell | 203/56 |
| 4,081,332 | 3/1978 | Hein | 203/56 |

OTHER PUBLICATIONS

The Soviet Chemical Industry, No. 11, Nov. 1971, pp. 719–723.

Primary Examiner—Wilbur L. Bascomb, Jr.
Attorney, Agent, or Firm—Keil & Witherspoon

[57] ABSTRACT

A process for isolating a conjugated diolefin from a C$_4$- or C$_5$-hydrocarbon mixture containing the diolefin, by single-stage or multi-stage extractive distillation using a selective solvent, wherein the selective solvent is a solvent mixture which comprises
 (a) from 1 to 99 percent by weight of an N-alkyl-substituted lower aliphatic acid amide or of an N-alkyl-substituted alicyclic acid amide having 5 ring members and
 (b) from 1 to 99 percent by weight of an aliphatic or alicyclic ether boiling at from 30° C. to 200° C.

3 Claims, No Drawings

ISOLATION OF A CONJUGATED DIOLEFIN FROM A $C_4$- OR $C_5$-HYDROCARBON MIXTURE

The present invention relates to a process for isolating a conjugated diolefin from a $C_4$- or $C_5$-hydrocarbon mixture by extractive distillation with the aid of a selective solvent.

Extractive distillation is a known process for separating mixtures which are not easily separable by conventional fractional distillation, for example if the components to be separated form an azeotrope or if the differences in the relative volatilities are slight. In extractive distillation, a solvent of relatively low volatility is introduced into the distillation column in such amounts that the differences in the relative volatilities of the components to be separated are increased and hence distillative separation becomes possible. Typical examples of the application of extractive distillation are to be found, for instance, in C.S. Robinson et al. "Elements of Fractional Distillation", 4th edition, McGraw-Hill Book Company, Inc., New York, (1959), page 291.

It is known, for example from German Published Application DAS No. 1,568,902, German Patent No. 1,163,795 or The Soviet Chemical Industry, No. 11, November 1971, pages 719-723, that conjugated diolefins can be isolated from a $C_4$- or $C_5$-hydrocarbon mixture by extractive distillation using a selective solvent. The selective solvents can be used substantially anhydrous. However, in this method, which is used especially in the case of solvents sensitive to hydrolysis, the $C_4$- or $C_5$-hydrocarbon selectivity is in general insufficient. Hence, water has been added to the selective solvents to increase the selectivity and to lower the boiling point. However, such addition of water to the selective solvent has the disadvantage that it reduces the solubility of the $C_4$- or $C_5$-hydrocarbons in the selective solvent, so that the amount of selective solvent circulating in the extraction unit is correspondingly increased.

It is an object of the present invention to provide a process for isolating a conjugated diolefin from a $C_4$- or $C_5$-hydrocarbon mixture containing the diolefin, by single-stage or multi-stage extractive distillation using a selective solvent, wherein the amount of selective solvent circulating in the extraction unit can be kept low.

According to the invention, this object and other objects and advantages are achieved by a process for isolating a conjugated diolefin from a $C_4$- or $C_5$-hydrocarbon mixture containing the diolefin, by single-stage or multi-stage extractive distillation using a selective solvent, wherein the selective solvent used is a solvent mixture which comprises (a) from 1 to 99 percent by weight of an N-alkyl-substituted lower aliphatic acid amide or of an N-alkyl-substituted alicyclic acid amide having 5 ring members and (b) from 1 to 99 percent by weight of an aliphatic or alicyclic ether boiling at from 30° C. to 200° C.

The solubility of the $C_4$- or $C_5$-hydrocarbons in the solvent mixture which according to the invention is to be used as the selective solvent is substantially increased compared to the solubility in the solvents used in the conventional processes, whilst the $C_4$- or $C_5$-hydrocarbon selectivity is similar, so that the amount of selective solvent circulating in the extraction unit for isolating the conjugated diolefin can be greatly reduced. This in particular results in a great reduction in the investment required for the extraction unit, and in the consumption of steam and electrical energy. Furthermore, the solvent mixture to be used according to the invention has a lower viscosity, a lower heat of vaporization and a lower specific heat than the conventional selective solvents of comparable $C_4$- or $C_5$-hydrocarbon selectivity. The lower viscosity of the solvent mixture to be used according to the invention results in a higher tray efficiency in the extractive distillation column, whilst as a result of the lower heat of vaporization and lower specific heat, energy can additionally be saved.

If a mixture of one of the relatively high-boiling solvents according to section (a) above with a solvent according to section (b) which is lower-boiling than the first-mentioned solvent is used, for example if the solvent according to section (b) boils below 150° C., preferably below 125° C., an additional advantage achieved is that the solvent recovery zone of the extraction unit for isolating the conjugated diolefin, which recovery zone is, for example, operated as a degassing zone or solvent stripping zone, can, for a given bottom temperature, be operated under higher pressure than is the case when using only the solvents according to (a) in accordance with conventional processes. This has the advantage, for example, that because of the higher pressure the degassed hydrocarbons obtained in the solvent recovery zone can, without interpolation of a compressor, be fed into downstream zones operated under higher pressure. Another advantage of using a mixture of one of the relatively high-boiling solvents according to (a) above with a lower-boiling solvent according to (b) above is that the solvent recovery zone of the extraction unit, which zone is, for example, operated as a degassing zone or solvent stripping zone, can, when using the same pressure as in conventional processes, be operated at a lower bottom temperature, so that contamination of the extraction unit by polymer formation can more easily be avoided.

The process according to the invention employs a solvent mixture which comprises (a) from 1 to 99 percent by weight of an N-alkyl-substituted lower aliphatic acid amide or of an N-alkyl-substituted alicyclic acid amide having 5 ring members and (b) from 1 to 99 percent by weight of an aliphatic or alicyclic ether boiling at from 30° C. to 200° C., preferably from 40° C. to 150° C., especially from 50° C. to 125° C.

Examples of suitable N-alkyl-substituted lower aliphatic acid amides are dimethylformamide, diethylformamide, dimethylacetamide, diethylacetamide and formylmorpholine. Examples of suitable N-alkyl-substituted alicyclic acid amides(lactams) are N-alkylpyrrolidones, especially N-methylpyrrolidone. In general, N-alkyl-substituted lower aliphatic acid amides or N-alkyl-substituted alicyclic acid amides boiling at from 150° C. to 260° C., preferably from 150° C. to 210° C., are used. It is particularly advantageous to use dimethylformamide and more especially still N-methylpyrrolidone as the solvent (a).

The solvent mixture to be used according to the invention contains from 1 to 99 percent by weight, preferably from 2 to 50 percent by weight, especially from 3 to 20 percent by weight, of one of the solvents according to (b) above. Correspondingly, the solvent mixture contains from 1 to 99 percent by weight, preferably from 50 to 98 percent by weight, especially from 80 to 97 percent by weight, of one of the solvents according to (a) above. If a solvent mixture containing N-methylpyrrolidone is used, it particularly advantageously contains from 7 to 17 percent by weight of one of the solvents according to (b) above.

Examples of suitable aliphatic ethers are symmetrical or unsymmetrical ethers of the general formula R—O—R′, where, in general, the aliphatic radical R is a hydrocarbon radical of 1 to 6, preferably 1 to 5, especially 1 to 4, carbon atoms and the aliphatic radical R′ is a hydrocarbon radical of 2 to 6, preferably 2 to 5, carbon atoms. The total number of carbon atoms of the two hydrocarbon radicals together is advantageously from 4 to 12, preferably from 5 to 10.

Examples of suitable radicals R and R′ are the ethyl, n-propyl, isopropyl, n-butyl, isobutyl and tert.-butyl radical, the amyl radicals and hexyl radicals, and R may also be methyl. Examples of suitable ethers are symmetrical ethers, eg. diethyl ether, di-n-propyl ether, diisopropyl ether, di-n-butyl ether, diisobutyl ether, di-n-amyl ether and diisoamyl ether and, preferably, unsymmetrical ethers, eg. methyl n-butyl ether, methyl tert.-butyl ether, ethyl tert.-butyl ether, n-propyl tert.-butyl ether, isopropyl tert.-butyl ether, isobutyl tert.-butyl ether, n-butyl tert.-butyl ether, methyl tert.-amyl ether, ethyl tert.-amyl ether, n-propyl tert.-amyl ether, isopropyl tert.-amyl ether, n-butyl tert.-amyl ether, isobutyl tert.-amyl ether, methyl isopropyl ether, ethyl isopropyl ether, n-propyl isopropyl ether, n-butyl isopropyl ether, isobutyl isopropyl ether and ethyl n-butyl ether. It is particularly advantageous to use those unsymmetrical ethers where one radical is a tert.-amyl or isopropyl group or especially a tert.-butyl group.

Examples of other suitable aliphatic ethers are the monoalkyl ethers and preferably dialkyl ethers of dihydric alcohols, such as the ethers of the general formula $R^1$—$[OCH_2$—$CHR]_n$O—$R^2$, where R is hydrogen or $CH_3$, $R^1$ and $R^2$ are each a hydrocarbon radical of 1 to 5, preferably 1 to 4, carbon atoms, and n is an integer from 1 to 3, preferably 1 or 2, and $R^1$ may also be hydrogen. Examples of dialkyl ethers of dihydric alcohols are ethylene glycol dimethyl ether, diethyl ether, di-n-propyl ether, diisopropyl ether, diisobutyl ether, methyl isopropyl ether and methyl tert.-butyl ether, diethylene glycol dimethyl ether and methyl isopropyl ether, 1,2-propylene glycol dimethyl ether and 1,4-butanediol dimethyl ether. Examples of suitable monoalkyl ethers of dihydric alcohols are ethylene glycol monomethyl ether, monoethyl ether, mono-n-propyl ether, monoisopropyl ether, mono-n-butyl ether and monoisobutyl ether, diethylene glycol monomethyl ether and diethylene glycol monoethyl ether.

Examples of alicyclic ethers, ie. cyclic ethers which do not contain any hetero-atoms other than oxygen atoms, are tetrahydrofuran, 2-methyltetrahydrofuran, 3-methyltetrahydrofuran, tetrahydropyran and 1,4-dioxane, of which tetrahydrofuran is preferred.

The solvent mixture to be used according to the invention can contain a small amount of water, for example up to 10 percent by weight. Advantageously, however, the water content is restricted to at most 5 percent by weight, preferably at most 3 percent by weight, based on the solvent mixture. However, it can be advantageous to employ a substantially anhydrous solvent mixture, ie. a mixture containing at most 1 percent by weight, preferably at most 0.5 percent by weight, in particular at most 0.1 percent by weight, of water, based on the solvent mixture.

The isolation of a conjugated diolefin from a $C_4$- or $C_5$-hydrocarbon mixture containing the latter, using the solvent mixture which according to the invention is employed as the selective solvent, is carried out in a conventional manner (cf., for example, German Pat. No. 1,184,334 and German Published Applications DAS No. 1,568,876 and 1,568,902) by single-stage or multi-stage, advantageously single-stage or two-stage, extractive distillation. For example, the conjugated diolefins, eg. 1,3-butadiene, isoprene and 1,3-pentadiene, are isolated from the $C_4$- or $C_5$-hydrocarbon mixture by subjecting the latter, which contains both hydrocarbons which are more soluble and hydrocarbons which are less soluble than the conjugated diolefin, to an extractive distillation with the solvent mixture to be used according to the invention, from which distillation a distillate containing the less soluble hydrocarbons and an extract containing the conjugated diolefin, the more soluble hydrocarbons and the selective solvent are obtained. The conjugated diolefin can be isolated, from the extract, in the form of a crude product which is of adequate purity for certain applications, but which can also be subjected to additional purification operations, for example fractional distillation. Advantageously, however, the conjugated diolefin is isolated by using two successive extractive distillation stages using the solvent mixture to be employed according to the invention.

Using the latter method, the first stage of the extractive distillation results, for example, as already described above, in a distillate containing the less soluble hydrocarbons and an extract containing the conjugated diolefin, the more soluble hydrocarbons and the selective solvent. This extract is freed from the selective solvent, giving a mixture of the conjugated diolefin and the more soluble hydrocarbons. This mixture is subjected to a second extractive distillation using the selective solvent, giving the conjugated diolefin as the distillate, and an extract which contains the more soluble hydrocarbons and the selective solvent. The extract obtained is subsequently freed from the selective solvent, giving a hydrocarbon stream containing the more soluble hydrocarbons.

The hydrocarbon mixture, containing conjugated diolefins, used as the starting mixture for the process of the present invention may be a $C_4$- or $C_5$-fraction which was obtained by thermal cracking of a petroleum fraction (for example LPG, naphtha and the like), a butadiene-containing fraction obtained by dehydrogenation of n-butane and/or n-butene, or an isoprene-containing fraction obtained by dehydrogenation of isopentane and/or isoamylene. In general, the $C_4$-hydrocarbon mixture contains 1,3-butadiene as the conjugated diolefin, together with butanes, n-butene, isobutene, vinylacetylene, ethylacetylene and 1,2-butadiene, with or without small amounts of $C_3$- and/or $C_5$-hydrocarbons. The $C_5$-hydrocarbon mixture as a rule contains isoprene, trans- and cis-1,3-pentadiene and cyclopentadiene as conjugated diolefins, together with pentanes, n-pentenes, isoamylene, cyclopentene and higher acetylenes.

By way of example, extractive distillation of a $C_4$-fraction first gives a distillate containing the butanes and butenes, and an extract containing 1,3-butadiene, ethylacetylene, vinylacetylene and 1,2-butadiene, which extract, when subjected to a further extractive distillation, gives 1,3-butadiene as the distillate, whilst the extract contains ethylacetylene, vinylacetylene and 1,2-butadiene. The ethylacetylene, vinylacetylene and 1,2-butadiene are separated from the extract, containing these hydrocarbons, in a degassing unit, and the degassed solvent is recycled to the extractive distillation. The 1,3-butadiene obtained as the distillate can subsequently be subjected to a fractional distillation to remove the very small amounts of $C_3$- and/or $C_5$-hydrocarbons which may still be present.

The Examples which follow illustrate the invention.

EXAMPLE 1

Example 1 illustrates the single-stage extractive distillation of a $C_4$-hydrocarbon mixture.

A packed column of 25 mm internal diameter and 2.50 m height, operated under 1 bar at 15° C., is fed, at the bottom, with 0.858 kg/h of a $C_4$-hydrocarbon mixture of the following composition:

| Composition | % by weight |
| --- | --- |
| i-Butane | 1.33 |
| n-Butane | 4.44 |
| But-1-ene | 11.65 |
| i-Butene | 28.21 |
| Trans-but-2-ene | 7.28 |
| Cis-but-2-ene | 4.45 |
| 1,3-Butadiene | 41.98 |
| 1,2-Butadiene | 0.31 |
| Ethylacetylene | 0.24 |
| Vinylacetylene | 0.11 |

At the top of the column, 4.60 kg/h of recycled selective solvent, containing 90% by weight of N-methylpyrrolidone and 10% by weight of methyl tert.-butyl ether, are introduced at 15° C. 0.418 kg/h of a raffinate containing 7.89% by weight of 1,3-butadiene and 4.78% by weight of cis-but-2-ene (key component for the separation) are taken off as gas at the top of the column. 1,2-Butadiene and the $C_4$-acetylenes (ethylacetylene and vinylacetylene) are no longer detectable in the raffinate. At the bottom of the column, an extract containing the more readily soluble hydrocarbons is taken off and is fed, for further separation and degassing, to the top of a downstream column which has 10 bubble-cap trays and is operated at a bottom temperature of 130°–140° C. From the bottom of the column, the selective solvent, which has been substantially freed from the hydrocarbons, is recycled, after cooling, to the top of the packed column. At the center of the bubble-cap tray column, 0.440 kg/h of crude butadiene containing 74.55% by weight of 1,3-butadiene and 4.09% by weight of cis-but-2-ene are taken off. The hydrocarbons issuing at the top of the bubble-cap tray column are recycled, as gas, to the bottom of the packed column.

COMPARATIVE EXPERIMENT

In a comparative experiment, the procedure described in Example 1 above is followed except that a mixture of 91.7% by weight of N-methylpyrrolidone and 8.3% by weight of water is used as the selective solvent, this solvent being fed to the packed column in a larger amount than in Example 1, namely 6.00 kg/h, and that the $C_4$-hydrocarbon mixture, having the same composition as in Example 1, is fed to the bottom of the packed column in a lower amount than in Example 1, namely 0.471 kg/h; 0.235 kg/h of raffinate and 0.236 kg/h of crude butadiene are obtained. Though, in the Comparative Experiment, the ratio of selective solvent fed in to $C_4$-hydrocarbon mixture fed in, namely 12.74, is 138% higher than the corresponding ratio in Example 1, namely 5.36, the Comparative Experiment gives, for virtually the same ratio of the amount of raffinate to the amount of crude butadiene (0.235/0.236) as in Example 1 (0.418/0.440), a raffinate having a 1,3-butadiene content of 14.77% by weight as against a 1,3-butadiene content of only 7.89% by weight in the raffinate according to Example 1. Furthermore, the key component cis-but-2-ene accumulates to a lesser degree in the raffinate of the Comparative Experiment (4.41% by weight of cis-but-2-ene) than in the raffinate of Example 1 (4.78% by weight of cis-but-2-ene). Whilst 1,2-butadiene, ethylacetylene and vinylacetylene are still clearly detectable in the raffinate from the Comparative Experiment, the contents of these components in the raffinate of Example 1 are below the limits of detectability. Furthermore, the crude butadiene obtained in the Comparative Experiment has a 1,3-butadiene content of only 69.07% by weight, compared to a figure of 74.55% by weight in Example 1. In addition, the content of cis-but-2-ene in the crude butadiene was reduced only to 4.66% by weight in the Comparative Experiment, whilst in Example 1 the corresponding value was 4.09% by weight.

EXAMPLE 2

The procedure described in Example 1 and the corresponding Comparative Experiment is followed, except that in Example 2 the selective solvent used is a mixture of 90% by weight of N-methylpyrrolidone and 10% by weight of tetrahydrofuran and an S/M ratio of circulating solvent S to feed M of $C_4$ hydrocarbon mixture of 6.50 is maintained, whilst in the Comparative Experiment accompanying Example 2 an S/M ratio of 12.74 is maintained to achieve the same degree of success in the separation. This means that to achieve the same success, the S/M ratio had to be 96% higher in the Comparative Experiment than in the Example.

We claim:

1. A process for isolating a conjugated diolefin from a $C_4$- or $C_5$-hydrocarbon mixture containing the diolefin, by extractive distillation using a selective solvent, wherein the selective solvent is a solvent mixture which comprises
   (a) from 50 to 98 percent by weight of an N-alkyl-substituted lower aliphatic acid amide or of an N-alkyl-substituted alicyclic acid amide having 5 ring members and
   (b) from 2 to 50 percent by weight of
      an aliphatic ether boiling at from 30° C. to 200° C. of the general formula R—O—R', where the aliphatic radical R is a hydrocarbon radical of 1 to 6 carbon atoms and the aliphatic radical R' is a hydrocarbon radical of 2 to 6 carbon atoms, or
      a dialkyl ether of a dihydric alcohol boiling at from 30° C. to 200° C. of the general formula $R^1$—[OCH$_2$—CHR—]$_n$ OR, where R is hydrogen or CH$_3$, $R^1$ and $R^2$ are each a hydrocarbon radical of 1 to 5 carbon atoms, and n is an integer from 1 to 3, or
      an alicyclic ether boiling at from 50° C. to 125° C.

2. A process as claimed in claim 1 wherein said N-alkyl-substituted lower aliphatic acid amide or said N-alkyl-substituted alicyclic acid amide is selected from the group consisting of dimethylformamide, diethylformamide, dimethylacetamide, diethylacetamide, formylmorpholine or N-methylpyrrolidone.

3. A process as claimed in claim 1 or 2, wherein the solvent mixture contains at most 5 percent by weight of water, based on solvent mixture.

* * * * *